United States Patent
Siversson (10) Patent No.: US 10,149,987 B2
(45) Date of Patent: Dec. 11, 2018

(54) METHOD AND SYSTEM FOR GENERATING SYNTHETIC ELECTRON DENSITY INFORMATION FOR DOSE CALCULATIONS BASED ON MRI

(71) Applicant: SPECTRONIC AB, Helsingborg (SE)

(72) Inventor: Carl Siversson, Råå (SE)

(73) Assignee: SPECTRONIC AB (SE)

( * ) Notice: Subject to any disclaimer, the term of this patent is extended or adjusted under 35 U.S.C. 154(b) by 0 days.

(21) Appl. No.: 15/309,017

(22) PCT Filed: May 4, 2015

(86) PCT No.: PCT/SE2015/050490
§ 371 (c)(1),
(2) Date: Nov. 4, 2016

(87) PCT Pub. No.: WO2015/171056
PCT Pub. Date: Nov. 12, 2015

(65) Prior Publication Data
US 2017/0072222 A1    Mar. 16, 2017

(30) Foreign Application Priority Data

May 4, 2014    (SE) .................................. 1430064
May 15, 2014   (SE) .................................. 1430070

(51) Int. Cl.
*A61N 5/10*    (2006.01)
*A61B 5/055*   (2006.01)
(Continued)

(52) U.S. Cl.
CPC ............ *A61N 5/1039* (2013.01); *A61B 5/055* (2013.01); *A61B 6/032* (2013.01); *A61B 6/037* (2013.01);
(Continued)

(58) Field of Classification Search
CPC ......... A61B 5/055; A61B 6/032; A61B 6/037; A61B 6/5247; A61B 6/563; A61N 5/1039;
(Continued)

(56) References Cited

U.S. PATENT DOCUMENTS

2006/0074293 A1    4/2006   Vilsmeier et al.
2007/0263769 A1    11/2007  Roell
(Continued)

OTHER PUBLICATIONS

Sjolund J. et al.: "Generating patient specific pseudo-CT of the head from MR using atlas-based regression", Physics in Medicine and Biology, Jan. 7, 2015, vol. 60, nr. 2, p. 825-839.
(Continued)

*Primary Examiner* — Ruth S Smith
(74) *Attorney, Agent, or Firm* — Condo Roccia Koptiw LLP (57) ABSTRACT

A method for generating synthetic electron density information based on an acquired magnetic resonance, MR, image stack is disclosed. The method comprises: analyzing the acquired MR image stack to automatically segment the acquired MR image stack; generating warp information for a template dataset comprising at least one template electron density information map and at least one template structure information, said generating comprising utilizing structure information of the acquired MR image stack and said template structure information in order to determine transformations bringing the template structures in spatial correspondence with the structures in the acquired MR image stack, wherein said generated warp information describes at least one transformation bringing the at least one template electron density information map in spatial correspondence with the acquired MR image stack; and forming synthetic electron density information corresponding to the acquired
(Continued)

MR image stack based on at least part of a warped template electron density information map.

14 Claims, 3 Drawing Sheets

(51) Int. Cl.
*A61B 6/03* (2006.01)
*A61B 6/00* (2006.01)
*G01R 33/48* (2006.01)
*G06T 7/33* (2017.01)
*G06T 7/11* (2017.01)
*G06T 7/00* (2017.01)

(52) U.S. Cl.
CPC ............ *A61B 6/5247* (2013.01); *A61B 6/563* (2013.01); *G01R 33/4808* (2013.01); *G06T 7/0012* (2013.01); *G06T 7/11* (2017.01); *G06T 7/337* (2017.01); *G06T 2200/04* (2013.01); *G06T 2207/10081* (2013.01); *G06T 2207/10088* (2013.01); *G06T 2207/20128* (2013.01); *G06T 2207/30004* (2013.01)

(58) Field of Classification Search
CPC ............ G01R 33/4808; G06T 2200/04; G06T 2207/10081; G06T 2207/10088; G06T 2207/20128; G06T 2207/30004; G06T 7/0012; G06T 7/11; G06T 7/337
See application file for complete search history.

(56) References Cited

U.S. PATENT DOCUMENTS

| 2011/0007959 A1 | 1/2011 | Schulz et al. |
| 2013/0121552 A1 | 5/2013 | Osztroluczki et al. |
| 2013/0266198 A1 | 10/2013 | Pereira et al. |
| 2014/0029823 A1 | 1/2014 | Birkbeck et al. |

OTHER PUBLICATIONS

Hofmann, M. et al.: "Towards quantitative PET/MRI: a review of MR-based attenuation correction techniques", European Journal of Nuclear Medicine and Molecular Imaging, Dec. 23, 2008, vol. 36, nr. 1, p. 93-104.

Hofmann, M. et al.: "MRI-Based Attenuation Correction for PET/MRI: A Novel Approach Combining Pattern Recognition and Atlas Registration", The Journal of Nuclear Medicine, Nov. 1, 2008, vol. 49, nr. 11, p. 1875-1883.

Dowling J. A. et al.: "Automatic Atlas Based Electron Density and Structure Contouring for MRI-based Prostate Radiation Therapy on the Cloud", Journal of Physics: Conference Series, Mar. 24, 2014, vol. 489, nr. 1.

Dowling, J. et al.: "Automatic MRI Atlas-Based External Beam Radiation Therapy Treatment Planning for Prostate Cancer", Prostate Cancer Imaging. Computer-Aided Diagnosis, Prognosis, and Intervention, Sep. 24, 2010, vol. 6367, p. 25-33.

METHOD AND SYSTEM FOR GENERATING SYNTHETIC ELECTRON DENSITY INFORMATION FOR DOSE CALCULATIONS BASED ON MRI

CROSS-REFERENCE TO RELATED APPLICATIONS

This application is the National Stage Entry under 35 U.S.C. § 371 of Patent Cooperation Treaty Application No. PCT/SE2015/050490, filed May 4, 2015, which claims priority to Sweden Application No. 1430064-4, filed May 4, 2014 and Sweden Application No. 1430070-1, filed May 15, 2014, the contents of which are hereby incorporated by reference in their entirety.

TECHNICAL FIELD

The following disclosure relates generally to the fields of medical imaging and radiation therapy and, more specifically, to the application of image processing techniques in a computer software tool for creating a synthetic electron density information from a magnetic resonance image (MRI), e.g. for use in radiation treatment planning for cancer.

BACKGROUND

Tomography refers to a technique for capturing a two-dimensional (2D) or three-dimensional (3D) cross-sectional image of an object, through the use of radiation or any kind of penetrating wave. Computed Tomography (CT) refers to a medical imaging technique that uses X-rays and computer processors to collect and display 2D or 3D images or tomograms of an object. Magnetic Resonance imaging (MRI) refers to a tomographic technique that uses a powerful magnetic field and a radio frequency transmitter to capture detailed images of organs and structures inside the body.

Radiation therapy refers to a technique where cancer tumors are controlled or killed by the application of high energy ionizing radiation. In the case of external radiation therapy the ionizing radiation is applied from outside the body from one or more directions, which are all directed towards the tumor to be treated. The ionizing radiation is often generated by a linear electron accelerator. The uptake of radiation by a tissue volume is referred to as the dose given to the tissue. A complete cancer treatment usually consists of several radiation therapy sessions, each of which is referred to as a fraction.

Radiation treatment planning refers to the step preceding the radiotherapy sessions, during which the application of radiation is carefully planned. Different organs and tissues exhibit different sensitivity to radiation. Organs and tissue for which the radiation will cause most negative side effects are referred to as risk organs. The area containing the tumor to be treated is referred to as the target. During radiation treatment planning the goal is to provide a specific dose to the target, while keeping it as low as possible to the surrounding risk organs. The means available for this are the angles from which the radiation is applied, together with the shape and strength of the radiation beam. In order to achieve this, the radiation treatment planning step is typically preceded by a tomographic step, which is then used for the identification and localization of target and risk organs.

Attenuation refers to the gradual loss of energy as a signal passes through a medium. In the context of CT, attenuation of the X-ray energy occurs as the X-rays pass through different tissues and structures in the body. The grayscale values in the CT image constitute an accurate representation of this attenuation at each location. Different tissues have different properties and densities and, thus, produce different amounts of attenuation. The attenuation coefficient describes the extent to which a particular material or tissue causes a loss of energy. In the context of radiotherapy, attenuation occurs as the radiation passes through the body and dose is absorbed by different tissues and structures.

In order to be able to accurately calculate the dose given to both target and risk organs, it is of high importance to know the exact energy deposition at every location through which the radiation passes. For this reason the tomography preceding the radiation treatment planning is traditionally CT, since there is a relation between the CT values and the dose deposition of the high-energy radiation used for radiotherapy.

Since a CT image constitutes a representation of X-ray attenuation, the primary contrasts within a CT image is that between bone, soft-tissue and air. Both between and within different types of soft-tissues (such as organs, muscles and fat), the image contrast is highly limited. During radiation treatment planning, this low contrast is a disadvantage, since it limits the accuracy by which target and risk organs can be identified.

Traditionally, radiation therapy planning specialists must often estimate and guess at the target and risk organ size and location based on their experience. Bony structures, or marker implants, provide the primary reference landmarks within the image. For this reason, the usual practice during planning is to "overstate" the area within the patient for subsequent radiation treatment. Thus, the radiation beam will be sure to hit the intended target. However, the disadvantage is that otherwise healthy tissue is thereby also unnecessarily irradiated.

For this reason, modern radiotherapy often also includes an additional MRI scan which is also performed prior to the radiation treatment planning, which has superior contrast between different soft tissues compared to the CT image. Such MRI scan is typically aligned to the CT scan and used in conjunction with the CT during the radiation treatment planning.

However, even such combined CT/MRI workflow has several disadvantages. First, acquiring both an MRI and a CT is both expensive and time consuming, and it also adds additional discomfort to the patient. Secondly, the registration between MRI and CT is rarely perfect, which adds an uncertainty to the identification of both the target and the risk organs. In addition, the CT itself adds a significant radiation dose to the patient, which limits its repeated use in following tumor changes between fractions.

Therefore, a solution which would enable an MRI-only workflow, and thereby eliminate the requirement of CT, in radiation treatment planning, is highly sought for.

US 2011/0007959 discloses a method, wherein co-registered CT and MRI anatomical structure reference images are used. When an MR image of a patient is acquired, a user can click and drag landmarks on the reference MR image to deform the reference MR image to align with the patient MR image. The registration of landmarks also registers the patient MR image with a corresponding landmark in the co-registered reference CT image. However, this method requires extensive user interaction in order to generate desired electron density information.

In Hofmann et al, "MRI-Based Attenuation Correction for PET/MRI: A Novel Approach Combining Pattern Recognition and Atlas Registration", Journal of Nuclear Medicine, 2008, volume 49, issue 11, pages 1875-1883, a method for using MRI in creation of synthetic CT, or attenuation correction information, which accounts for radiation-attenuation properties of the tissue. The method uses a non-rigid registration algorithm for aligning a template MR image with a new subject's MR image. This alignment is then used to compute a desired result from a template CT image.

SUMMARY OF THE INVENTION

With the above description in mind, then, an aspect of some embodiments of the present invention is to provide a method for generating synthetic CT image stacks for use in radiation treatment planning, which seeks to mitigate, alleviate or eliminate one or more of the above-identified deficiencies in the art and disadvantages singly or in any combination.

According to a first aspect of the invention, there is provided a method for generating synthetic electron density information based on an acquired magnetic resonance, MR, image stack, said method comprising: analyzing the acquired MR image stack in order to automatically segment the acquired MR image stack such that structure information defining locations and/or geometry of structures in the acquired MR image stack is determined; generating warp information for a template dataset, said template dataset comprising at least one template electron density information map and at least one template structure information, said generating comprising utilizing said structure information and said template structure information representing locations and/or geometry of template structures in order to determine transformations bringing the template structures in spatial correspondence with the structures in the acquired MR image stack, wherein said generated warp information describes at least one transformation bringing the at least one template electron density information map in spatial correspondence with the acquired MR image stack; and forming synthetic electron density information corresponding to the acquired MR image stack based on at least part of the at least one template electron density information map, wherein the at least part of the at least one template electron density information map is warped using the generated warp information.

According to the method, segmentations defining information about structures in image stacks are used for relating a template to the acquired MR image stack. Hereby, the locations and/or geometry of structures drive the determination of transformations that would bring the template structures in spatial correspondence with the structures in the acquired MR image stack. This implies that it is not necessary to use a template MR image stack which is to be first registered to the acquired MR image stack, before the relation of the template electron density information map to the acquired MR image stack may be determined.

Using the segmentation for generating the warp information also enables bringing template electron density information maps into spatial correspondence with the currently acquired MR image stack, even though the template electron density information maps and the currently acquired MR image stack may be acquired from different persons with highly different geometries. Thanks to the segmentation, the template electron density information maps may still be accurately related to the acquired MR image stack and may thus provide valuable information for forming the synthetic electron density information.

According to a second aspect of the invention, there is provided a system for generating synthetic electron density information based on an acquired magnetic resonance, MR, image stack, said system comprising: an automatic segmentation module, which is configured to analyze the acquired MR image stack such that structure information defining locations and/or geometry of structures in the acquired MR image stack is determined; a warp module, which is configured to generate warp information for a template dataset, said template dataset comprising at least one template electron density information map and at least one template structure information, said generating comprising utilizing said structure information and said template structure information representing locations and/or geometry of template structures in order to determine transformations bringing the template structures in spatial correspondence with the structures in the acquired MR image stack, wherein said generated warp information describes at least one transformation bringing the at least one template electron density information map in spatial correspondence with the acquired MR image stack; and a forming module, which is configured to form synthetic electron density information corresponding to the acquired MR image stack based on at least part of the at least one template electron density information map, wherein the at least part of the at least one template electron density information map is warped using the generated warp information.

Thus, a system facilitating generation of synthetic electron density information is provided. The system may be set up in a remote location, such that when an MR image stack is acquired at a hospital, the MR image stack may be received by the system and synthetic electron density information may be returned. This implies that hospitals may benefit from a large number of gathered templates, which may be continuously improved and provided with further templates, and the individual hospitals need not gather their own templates.

However, it should be realized, that the system may also be set up locally, e.g. within a hospital. This may provide simpler handling of information as less restrictive data encryption and patient de-identification strategies may be allowed, as compared to information being transmitted to a system outside the hospital.

As used herein, the term "electron density information" should be construed as information that enables calculation of the absorbed radiation dose in an object. For instance, this could be a CT image stack, which constitutes a representation of Hounsfield values. However, when radiotherapy is applied, high-energy photon, proton or electron radiation is typically used and the information provided by the CT image stack may need to be transformed in order to give the absorbed radiation dose. Thus, the electron density information may alternatively be information more directly describing properties relevant to radiation used in radiotherapy, and the term "electron density information" should thus be construed to include such information. For certain types of radiation treatment, e.g. protons, this information may be in the form of stopping power maps, which also falls within the meaning of the term "electron density information" as used herein.

According to one embodiment, the synthetic electron density information is in the form of a synthetic CT image stack and the at least one template electron density information map is a template CT image stack.

As used herein, the term "image stack" should be construed as any representation of image information that collectively represents three-dimensional information of an imaged object.

It should be realized that the template structure information need not necessarily be transformed to be brought in spatial correspondence with the structures in the acquired MR image stack. In particular, it is not necessary to transform the template electron density map. It may be sufficient to determine the transformation that would bring the template electron density map to such spatial correspondence. Such determination forms information about the relation between the template structure and the acquired MR image stack, which information may be used as input to how synthetic electron density information is to be formed from the at least one template electron density information map.

Further, the template electron density information maps need not necessarily be warped using the warp information. Rather, a decision on which parts of a template electron density information map that is to be part of forming the synthetic electron density information may be taken, and then these parts may be warped when the synthetic electron density information is formed.

The synthetic electron density information may be formed based on a single template electron density information map. This may be especially useful e.g. when the template electron density information map is based on the same patient as the acquired MR image stack.

According to an embodiment, a set of template electron density maps are used and said generated warp information describes transformations bringing each template electron density information map in the set of template electron density information maps in spatial correspondence with the acquired MR image stack, wherein said forming comprises fusioning at least parts of the template electron density information maps, wherein the at least parts of the template electron density information maps are warped using the warp information, to form synthetic electron density information corresponding to the acquired MR image stack.

This implies that a plurality of template electron density maps may be used for contributing to the synthetic electron density information. Also when using a plurality of template electron density maps, the template electron density information maps need not be warped before fusioning. Rather, only the parts that are to be fused may be warped.

It should be realized that a plurality of template electron density maps may be included in the template dataset, whereas the set of template electron density maps used may be a subset of the plurality of template electron density maps. The template structure information may be provided in several different ways and may accordingly be related to the template electron density information maps in different ways.

In one embodiment, the template electron density information maps may be previously segmented in order to comprise template structure information providing locations and/or geometry of template structures within the template electron density information map. In such case, the determined transformation(s) bringing the template structures in spatial correspondence with the structures in the acquired MR image stack may be equal to transformation(s) that would bring the template electron density information map in spatial correspondence with the acquired MR image stack.

In another embodiment, separate template structure information is provided, which represents the locations and/or geometry of template structures. The template structure information may be related to the template electron density information map to describe how the template structures according to the template structure information correspond to the template electron density information map. Thus, the determined transformation(s) bringing the template structures in spatial correspondence with the structures in the acquired MR image stack may then contribute to determining warp information that describes at least one transformation bringing the at least one template electron density information map in spatial correspondence with the acquired MR image stack.

In another embodiment, the template dataset further comprises at least one template MR image stack and said generating of warp information comprises determining spatial deformations of the at least one template MR image stack, said spatial deformations bringing the at least one template MR image stack in spatial correspondence with the acquired MR image stack, wherein the at least one template MR image stack has been segmented to identify template structure information representing locations and/or geometry of structures in the at least one template MR image stack, said spatial deformations comprising utilizing the structure information of the acquired MR image stack and the template structure information in order to bring the structures of the at least one template MR image stack to spatial correspondence with corresponding structures of the acquired MR image stack; and wherein the at least one template electron density information map is associated to respective ones of the at least one template MR image stack to define spatial and geometric relation between the at least one template MR image stack and the at least one template electron density information map, said generated warp information being based on the determined spatial deformation and said spatial and geometric relation.

Hence, template MR image stacks may be used, which are provided or related to template structure information. This implies that a spatial deformation may first be determined based on bringing the template structure information related to the template MR image stack in spatial correspondence with corresponding structures of the acquired MR image stack. Then, the warp information may be generated based on a further spatial and geometric relation between the template electron density information map and the template MR image stack.

The template MR image stacks need not be actually deformed to bring the template structure information related to the template MR image stack in spatial correspondence with corresponding structures of the acquired MR image stack. However, in one embodiment, the template MR image stack is spatially deformed in order to bring the template MR image stack in spatial correspondence with the acquired MR image stack. Thus, the determining of spatial deformations may actually include deforming the template MR image stacks.

In one embodiment, generating warp information comprises warping the template electron density information maps. This warping may generate candidate electron density information maps, which may then be used in fusioning for forming the synthetic electron density information maps.

The template electron density information maps may be associated to the template MR image stacks to provide a relation between a template electron density information map and its respective template MR image stack. In this regard, the template electron density information map may be registered to the template MR image stack. However, it should be realized that, instead of ensuring that the template electron density information map is registered to the template MR image stack, information defining the relation between the electron density information map and its respective template MR image stack may be provided. In such case, the warp information may be partly based on the relation between the template electron density information map and its respective template MR image stack in order to calculate how the template electron density information map relates to the acquired MR image stack.

In one embodiment, the template electron density information maps and the template MR image stacks are associated in pairs. The pairs may have been acquired from the same person. However, it should be realized that two or more template electron density information maps may be related to the same template MR image stack, or vice versa.

As used herein, the term "spatial correspondence" should be construed as the template structures represented by the template structure information and the acquired MR image stack being arranged so that like structures are either similarly placed or both similarly placed and similarly shaped. The template structures and the acquired MR image stack may thus be arranged to share a common coordinate system. The "spatial correspondence" may, at least in some embodiments, also imply that patterns or visual features in a template image (template electron density map or template MR image stack) are matched to patterns in the acquired MR image stack and brought in correlation where a high overlap is achieved between the patterns. Further, the term "spatial correspondence" should not be construed as template structures necessarily being in exact alignment with the acquired MR image stack. In fact, parts of the template structures may not be exactly matched with the acquired MR image stack, in particular, if a template MR image stack and the acquired MR image stack are acquired from different persons.

The warp information may comprise non-rigid transformation of the at least one template electron density information map. Such transformation allows the template electron density information map to be e.g. plastically or elastically deformed to achieve a high spatial correspondence between the template electron density information map and the acquired MR image stack.

The fusioning of at least parts of the template electron density information maps may use different parts from different template electron density information maps, on which the warp information has been applied, in order to stitch these warped parts together to form synthetic electron density information. In an embodiment, the fusioning may use as small parts as single pixels from the template electron density information maps. However, the fusioning may alternatively use partly or completely overlapping parts of the template electron density information maps in order to combine the information from one or more template electron density information maps into a part of the synthetic electron density information. Further, the fusioning may use entire template electron maps.

In one embodiment, fusioning may comprise, for each voxel location in the synthetic electron density information map to be formed, calculating a median value for each warped template electron density information map.

In another embodiment, fusioning may comprise utilizing expectation maximization algorithms to estimate a most likely value at each voxel location in the synthetic electron density information map.

In another embodiment, fusioning may comprise using a local image similarity metric, providing a measure of a correspondence between a spatially deformed template MR image stack and the acquired MR image stack. In such case, the fusioning may comprise, for each voxel location in the synthetic electron density information map to be formed, selecting a value from the warped template electron density information map corresponding to the spatially deformed template MR image stack having the highest similarity to the acquired MR image stack according to the local image similarity metric.

According to one embodiment, the analyzing of the acquired MR image stack is made in order to identify locations and/or geometry of at least one of or a part of: bone and skeleton parts, fat, muscle tissue, inner organs, intestines, bowels, colon, bladder, reproductive organs, brain regions, eyes, cochlea, sinuses, spine, mouth, nerves, glands, blood vessels, lungs, airways, heart, tumours or metastases. It should however be realized that any part or structure of a body may be identified in the acquired MR image and that the above is not an exclusionary list. According to one embodiment, the analyzing of the acquired MR image stack is made in order to identify locations and/or geometry of any type of markers, implants or prostheses (e.g. hip prosthesis, gold markers). According to yet another embodiment, the analyzing of the acquired MR image stack is made in order to identify locations and/or geometry of any type of resection cavity or other effect from previous treatments or traumas.

According to one embodiment, the analyzing of the acquired MR image stack may comprise a template-based method for automatically segmenting the acquired MR image stack.

According to one embodiment, utilizing the information of locations and/or geometry of structures in the acquired MR image stack and the template MR image stacks comprises performing non-rigid form transformation between locations and/or geometry of structures in the acquired MR image stack and the template MR image stacks.

According to one embodiment, the generated warp information comprises deformation fields utilized in the transformations bringing the at least one template electron density information map in spatial correspondence with the acquired MR image stack.

The deformation fields need not provide information describing transformations of each part of the template electron density information map. The generated warp information may also include transformation matrices describing transformations of one or several parts of the template electron density information map. Between parts for which any such transformation is described, interpolation may be applied.

According to an embodiment, the system further comprises a database in which the at least one template density information map and the at least one template structure information are stored.

According to an embodiment, the method further comprises accessing a database in which template data is stored, and selecting a set of data from the database to constitute the template dataset.

The set of template data that is selected from the database may be a sub-set of all template data that is stored in the database. The set of template data may thus be selected such that relevant template electron density information maps may be retrieved. According to one embodiment, the selected set of template electron density information maps forms a representative population of a region that is imaged in the acquired MR image stack.

According to one embodiment, the template data is stored in the database in association with information about a person, and the selection of the data to constitute the template dataset is based on a combination of information including: gender, age, weight, ethnicity, body mass index (BMI), pathology, or other parameters.

According to one embodiment, the template MR image stacks and associated template electron density information maps are arranged in close geometric registration to each other. The template MR image stacks and associated template electron density information maps may be thoroughly analyzed in order to bring them in close geometric registration to each other. The analysis may be manually, semi-automatically or automatically performed.

As used herein, the term "template MR image stack" should be construed as an image stack comprising MR information, but which does not necessarily have to be directly acquired from an MRI scanner. The template MR image stack may be a synthetic image stack that is generated by combining and/or improving one or more MR image stacks. For instance, each template MR image stack may be an average image stack based on a plurality of acquired MR image stacks.

Further, it should be realized that any data in a template dataset may be arranged in a common data structure and need not form separate data structures. Thus, a data structure in the form of a vector comprising a plurality of the data in the template dataset may form the template dataset.

According to one embodiment, the determining of said spatial deformations further comprises, after said utilizing, improving the spatial correspondence of the template MR image stacks with the acquired MR image stack by applying non-rigid image registration between the at least one template MR image stack and the acquired MR image stack. This implies that the determining of spatial deformations may comprise both using segmentation of structures in the acquired MR image stack and the template MR image stack and using an image registration technique. Hence, a very accurate spatial correspondence between the template MR image stack and the acquired MR image stack may be determined.

It should be realized that such improving of the spatial correspondence may also be performed directly between a template electron density information map and the acquired MR image stack, and need not necessarily be applied to a template MR image stack that the template electron density information map is associated with.

According to a third aspect of the invention, there is provided a computer program product comprising a computer-readable medium with computer-readable instructions such that when executed on a processing unit the computer program product will cause the processing unit to perform the method according to the first aspect of the invention.

According to a fourth aspect of the invention, there is provided a data structure comprising synthetic electron density information which is obtained by the method according to the first aspect of the invention.

According to a separate aspect of the invention, which need not be combined with other features previously described, such as automatic segmentation, there is provided a method for generating synthetic electron density information based on an acquired magnetic resonance, MR, image stack, said method comprising: determining spatial deformations of a set of template MR image stacks, said spatial deformations bringing each of the template MR image stacks in spatial correspondence with the acquired MR image stack, wherein said determining of spatial deformations generates warp information, wherein the warp information describes transformations bringing each template MR image stack in spatial correspondence with the acquired MR image stack, applying the generated warp information to a set of template electron density information maps, wherein the template electron density information maps are associated to respective ones of the template MR image stacks to form correlations between template MR image stacks and template electron density information maps, said applying providing a description of a warping of the template electron density information maps using the warp information; and fusioning at least parts of the template electron density information maps, wherein the at least parts of the template electron density information maps are warped using the warp information, to form synthetic electron density information corresponding to the acquired MR image stack.

According to this separate aspect, there is provided a set of template MR image stacks and a set of template electron density information maps that are associated to the template MR image stacks. When an MR image stack of a patient is acquired, the set of templates can thus be used for forming synthetic electron density information, whereby there is no need to acquire information that can be more directly related to the absorbed dose in the patient, such as a CT image stack. The set of template MR image stacks and the set of template electron density information maps may comprise a great amount of templates such that the acquired MR image stack can be compared to a large number of previously acquired templates in order to determine synthetic electron density information for the patient. By means of fusioning of the information from the template electron density information maps, synthetic electron density information of good quality may be obtained from the acquired MR image stack even though numerous templates or parts of the templates may not be very similar to the acquired MR image stack.

For instance, the templates need not be acquired from the same patient as the acquired MR image stack. This may also imply that a patient that is to undergo radiation treatment need not be exerted to radiation doses for acquiring information for radiation therapy planning.

BRIEF DESCRIPTION OF THE DRAWINGS

These and other aspects of the present invention will now be described in further detail, with reference to the appended drawings showing embodiment(s) of the invention.

DETAILED DESCRIPTION

Embodiments of the present invention relate, in general, to the field of generating synthetic electron density information. The forming of synthetic electron density information may be particularly useful for MRI based radiation treatment planning. However, it should be realized that it may be used in other applications as well. For instance, the synthetic electron density information may be used as attenuation information for a positron emission tomography (PET) camera or a single-photon emission computed tomography (SPECT) camera.

A preferred embodiment relates to generating synthetic CT image stacks for radiation dose calculation in cancer radiotherapy, such as prostate treatments, based on one or more MRI image stacks. However, it should be appreciated that the invention is as such equally applicable to radiotherapy in any other anatomical area, such as brain, head/neck, lungs, uterus, abdomen, or any other region in which radiation treatment planning is required. Likewise, it should be appreciated that the invention is not limited to human radiotherapy only, but is equally applicable with any species for which radiation treatment planning is required. However, for the sake of clarity and simplicity, the invention is mainly described below in relation to embodiments relating to forming synthetic CT image stacks for use in human radiation therapy planning.

Embodiments of the present invention will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference signs refer to like elements throughout.

In this context the term "registration" refers to the process of aligning a source image to a destination image, such that the source image is brought into the same coordinate system as the destination image, with as high overlap between visual features in the images as is possible. The term "rigid registration" refers to a registration process where the maximum overlap is achieved only by moving and rotating the source image relative to the destination image. The term "similitude registration" refers to a registration similar to a rigid registration, but with an additional scaling of the source image included. The term "non-rigid registration" refers to a registration process where the source image is e.g. plastically or elastically deformed to achieve the best possible overlap between the source and the destination images. The measurement by which the overlap between the images is measured is referred to as the "similarity metric". Common similarity metrics used in image processing include cross correlation, mutual information and sum of squared difference.

Figure 1:
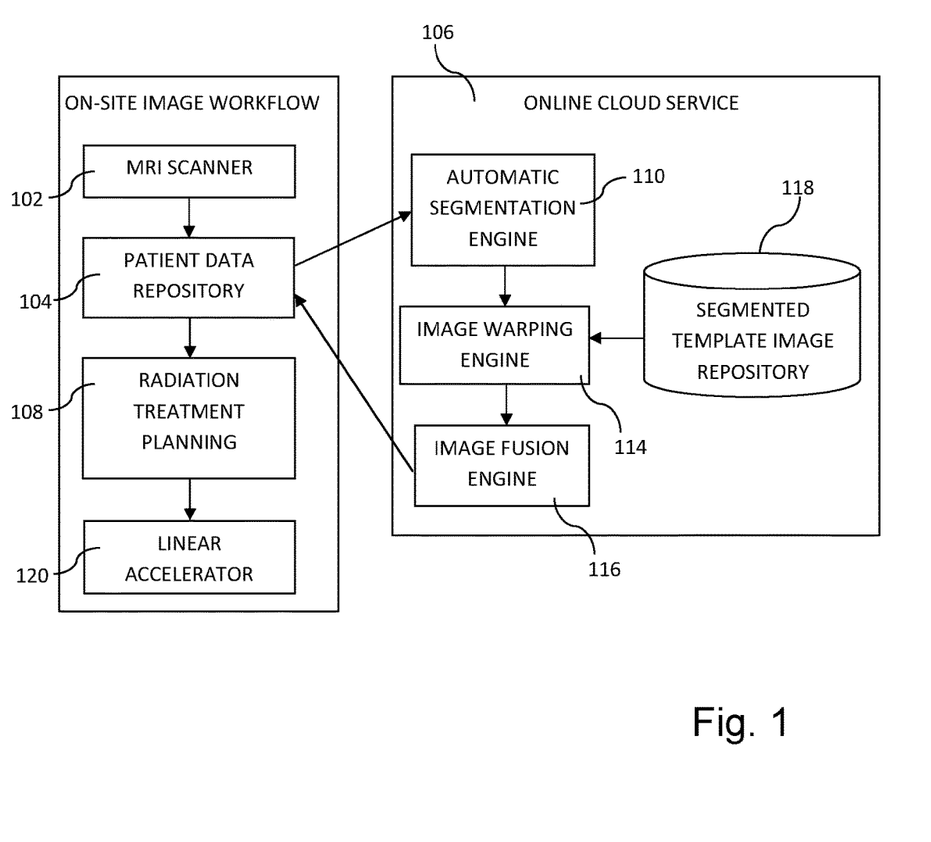
FIG. 1 is a schematic view showing an exemplary system for generating synthetic electron density information.

In this context the term "warping" refers to the process of deforming an image such that shape, size and location of structures and features within an image may be changed, Exemplary Synthetic CT System In FIG. 1 one embodiment in which the invention is used is shown. This embodiment of the synthetic CT system may typically comprise an MRI scanner 102, a Patient Data Repository 104, a system 106 for generating synthetic CT image stacks, to which system 106 image stacks are sent and received from the Patient Data Repository, a Radiation Treatment Planning module 108 and finally a Radiotherapy module. The system 106 to which image stacks are sent and received may comprise an Automatic Segmentation Engine 110, an Image Warping Engine 114, an Image Fusion Engine 116 and a Segmented Template Image Repository 118. Each of the elements in FIG. 1 may be embodied in hardware, software or computing instructions.

The Patient Data Repository 104, in some embodiments, may be configured to store raw image data obtained from the MRI scanner 102 or from other sources, and may include other images, computing instructions, and other associated parameters such as image types, regions, weights, values and characteristics. The Patient Data Repository 104 may include any type of memory for storing images, such as a static memory, magnetic memory, random access memory, non-volatile memory, volatile memory, magnetic storage, optical storage, and the like. The Patient Data Repository 104 is optionally configured to communicate with any or all of the MRI scanner 102, software of the Radiation Treatment Planning module 108 and a Linear Accelerator 120 implementing the Radiotherapy module. The communication may be through a direct connection, over a computing network, or through an alternative communication method.

Radiation Treatment Planning includes the process of manually or automatically delineating target and risk organs on tomographic image stacks, followed by forward or inverse treatment planning, using static or dynamic radiation beams, in combination with static or modulated beam shape (using techniques such as Volumetric Modulated Arc Therapy (VMAT) and Intensity-Modulated Radiation Therapy (IMRT)). A workstation executing Radiation Treatment Planning may utilize any software, from any vendor, for radiation treatment planning (for example software such as Eclipse, Raystation, Monaco or MasterPlan).

The Linear Accelerator 120 may deliver high energy photon radiation which kills tumor cells. The delivery of the radiation carefully follows the previously made dose plan, and may be accompanied by an additional imaging step to account for patient specific variation at the time of irradiation. All communications may utilize standardized file formats such as files meeting the Digital Imaging and Communications in Medicine (DICOM) standard, e.g. DICOM files and DICOM-RT files, for exchange of image stacks and other data.

The system 106 for generating synthetic CT image stacks may be implemented in a computing unit, such as a server, which may be connected to a computer network for allowing communication between the system 106 and the Patient Data Repository 104. In an embodiment, the system 106 may be implemented as an online cloud-computing platform. The system 106 may be accessible over the Internet and may utilize standardized communication means for sending data to and from the Patient Data Repository 104. Communications may be encrypted and the communicated data may be anonymized. In order to re-identify data as it is sent from the online platform to the Patient Data Repository 104, a client software may be running within the same network as the Patient Data Repository 104, which holds the keys required for re-identifying data belonging to previously anonymized patients.

The cloud-computing platform may further comprise software modules that generate the synthetic CT which may be used for dose calculations in radiation treatment planning. An incoming MR image stack may be received from a Patient Data Repository 104. The incoming image stack may automatically be segmented in several anatomical regions by the Automatic Segmentation engine 110. The incoming image stack, together with the automatically generated segments and a set of template electron density maps with previously created segments from a Segmented Template Image Repository 118, may be processed using the Image Warping Engine 114 into a set of candidate synthetic CT image stacks. The candidate synthetic CT image stacks may then be fused using the Image Fusion Engine 116 into a final synthetic CT image stack which corresponds to the incoming MR image stack. The synthetic CT image stack may form a data structure that is returned to the Patient Data Repository 104 using the communication means previously described. Optionally, the synthetic CT image stack may be returned to one or several Patient Data Repositories, which may be other repositories than the one the incoming MR image stack was received from. In this context, a Patient Data Repository may refer to any location where medical images are saved, either permanently or temporarily, including Hospital Information System (HIS), Radiology Information System (RIS), Picture Archiving and Communication System (PACS), network drives, Radiotherapy planning databases, local hard drives, Universal Serial Bus (USB) sticks, compact disc (CD), digital versatile disc (DVD), online storage, mobile devices, etc.

In another embodiment of the invention, the Automatic Segmentation Engine 110, the Image Warping Engine 114, the Image Fusion Engine 116 and the Segmented Template Image Repository 118 are running on a local computer or compute cluster on the same local network as, or otherwise directly connected to, the Patient Data Repository 104. The computing may optionally be performed using central processing unit (CPU), graphics processing unit (GPU), field-programmable gate array (FPGA), application specific integrated circuit (ASIC) or any other type of computing resources implemented either in software or hardware. The Automatic Segmentation Engine 110, the Image Warping Engine 114, the Image Fusion Engine 116 and the Segmented Template Image Repository 118 may be executed on a common such computing resource or may be separated on one or more different computing resources.

In one embodiment, a computer program product is provided for bringing a processing unit to implement the Automatic Segmentation Engine 110, the Image Warping Engine 114, and the Image Fusion Engine 116. The computer program product may thus be installed on any suitable processing unit for executing the functionality of the modules.

In yet another embodiment of the invention, all or any of the Automatic Segmentation Engine 110, the Image Warping Engine 114, the Image Fusion Engine 116 and the Segmented Template Image Repository 118 are integrated with either the MRI Scanner 102, the Patient Data Repository 104, the Radiation Treatment Planning module 108, the Linear Accelerator 120 or any combination thereof.

In another embodiment of the invention, the radiation for radiotherapy in the Radiotherapy module is optionally generated using a synchrotron. In yet another embodiment of the invention, the radiation for radiotherapy is generated by a radioactive isotope positioned at a number of locations outside the body. In yet another embodiment of the invention, radiation for radiotherapy is delivered using radioactive isotopes located inside the body (i.e. brachytherapy). The radiation used for radiotherapy in this invention may be of any type (i.e. photon, proton, electron, etc.).

In another embodiment, the synthetic CT image stack may be generated by registering a set of template MR image stacks, which may come from the Segmented Template Image Repository 118, to the incoming MR image stack. This may be followed by warping a corresponding set of template CT image stacks, which may come from the Segmented Template Image Repository 118, using deformation fields generated by the previous registrations, thereby generating a set of candidate synthetic CT image stacks which may be fused to a final synthetic CT image stack using the Image Fusion Engine 116. Each pair of template CT and template MR image stacks are first brought into alignment and may depict the same region of the same person.

Details of the parts of the system 106 for generating synthetic CT image stacks will now be further described.

Automatic Segmentation Engine

The Automatic Segmentation Engine 110, in some embodiments, comprises software algorithms to automatically label anatomical structures within the incoming MR image stack. Such structures may include, but is not limited to, bone and skeleton parts, fat, muscle tissue, inner organs, intestines, bowels, colon, bladder, reproductive organs, brain regions, eyes, cochlea, sinuses, spine, mouth, nerves, glands, blood vessels, lungs, airways, heart, tumours or metastases, any type of markers, implants or prostheses (e.g. hip prosthesis, gold markers), or any type of resection cavity or other effect from previous treatments or traumas.

Figure 2:
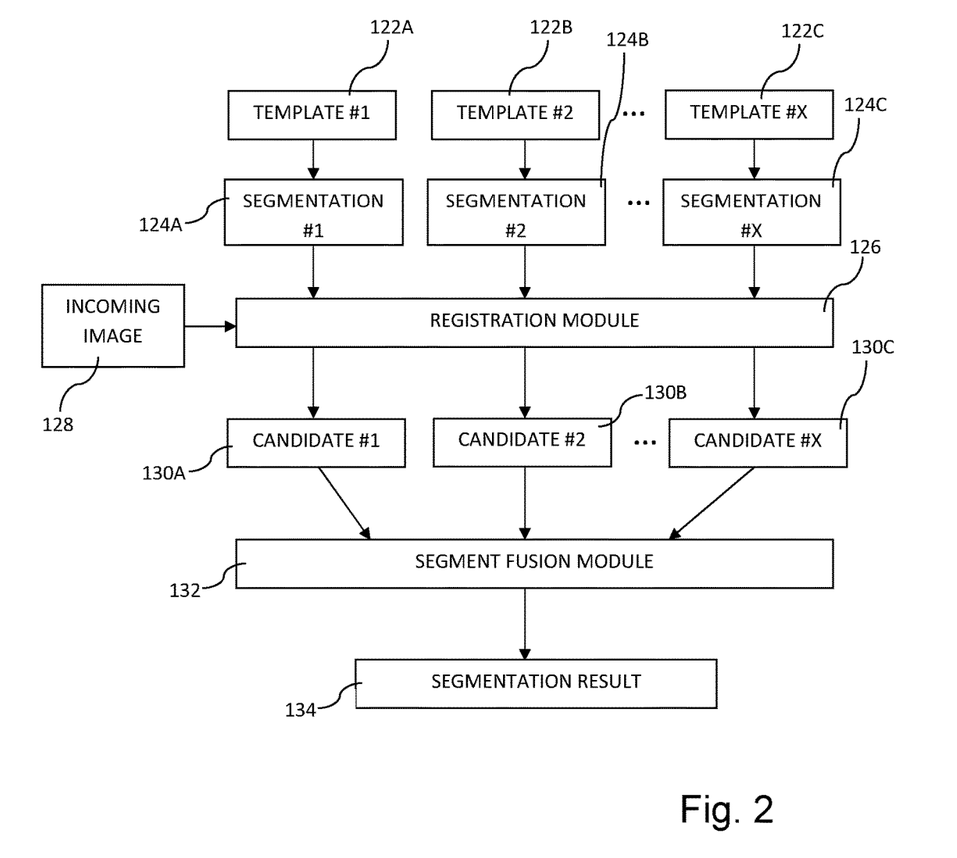
FIG. 2 is a schematic view illustrating an embodiment of an Automatic Segmentation Engine.

In FIG. 2 one embodiment of the Automatic Segmentation Engine 110 is shown. In order to aid automatic segmentation a number of template image stacks 122a-c are segmented in beforehand to form segmented template image stacks 124a-c. Each of a number of the previously segmented template image stacks 124a-c is registered using a registration module 126 to an incoming MR image stack 128. The template segmentations 124a-c may be generated manually by one or several raters, or otherwise generated through other manual, semi-automatic and automatic processes. The segmented template image stacks 124a-c may constitute a subset of the data from the Segmented Template Image Repository 118. The registration may be performed using any combination of rigid, similitude, affine or non-rigid registration methods. Each of the registrations may generate a deformation field, which may be applied to the segmentation which corresponds to the registered template, thereby generating segmentation candidates 130a-c representing the incoming MR image stack. All generated segmentation candidates 130a-c may then be fused by a segment fusion module 132 to a final segmentation 134 representing the incoming MR image stack 128. Such fusion method may be of a plurality of types, including majority voting, varieties of weighted voting, expectation maximization based label fusion etc.

In other embodiments the Automatic Segmentation Engine 110 may be based on an active contour model, active shape model, active appearance model, or any other segmentation technique. In yet another embodiment the Automatic Segmentation Engine 110 may utilize neural networks or other machine learning techniques during the segmentation process. In yet another embodiment, the automatically generated results may be verified and adjusted manually. In yet another embodiment, the Automatic Segmentation Engine 110 may utilize a combination of any of the mentioned techniques during the segmentation process. The Automatic Segmentation Engine 110 may utilize all or a subset of any image stack, or any features derived thereof, during the segmentation process.

Segmented Template Image Repository

The Segmented Template Image Repository 118, in some embodiments, comprises tomographic image stacks for a number of persons. For each person MR and correlated CT image stacks may be stored in the repository, which both may cover the same anatomical region and for which the CT image stack may be warped such that its structures accurately overlap that of the MRI stack to which it is correlated. The warping may be achieved using a combination of automated registration techniques, or based on manual interaction, or from a combination thereof. The warping may be represented as a transformed image stack. However, the CT image stack need not be actually warped to be in registration with the MR image stack. Rather, information regarding the spatial and geometric relation between the CT image stack and MR image stack may be stored, e.g. as a set of deformation parameters.

For each person a number of anatomical structures may be segmented. Such structures may include, but is not limited to, bone and skeleton parts, fat, muscle tissue, inner organs, intestines, bowels, colon, bladder, reproductive organs, brain regions, eyes, cochlea, sinuses, spine, mouth, nerves, glands, blood vessels, lungs, airways, heart, tumours or metastases, any type of markers, implants or prostheses (e.g. hip prosthesis, gold markers), any type of resection cavity or other effect from previous treatments or traumas, etc. Such segmentations may be generated manually by one or several persons, or otherwise generated through other manual, semi-automatic and fully automatic processes.

The Segmented Template Image Repository 118 need not comprise template MR image stacks. The CT image stacks may be provided with information defining locations and/or geometry of structures within the CT image stack. As a further alternative, separate template structure information, which need not be residing within a MR image stack or a CT image stack, may be provided.

In one embodiment of the Segmented Template Image Repository 118, the image stacks which are utilized are selected based on any combination of gender, age, weight, ethnicity, body mass index (BMI), pathology or any other parameter which may affect the results.

In one embodiment of the Segmented Template Image Repository, the previously described warping is instead performed from the MR image stack to the CT image stack.

In yet another embodiment, the image stacks in the Segmented Template Image Repository 118 are, fully or partially, synthetically generated based on features derived from images of real persons.

Image Warping Engine

The Image Warping Engine 114, in some embodiments, uses any template structure information, which may be stored with the CT image stacks or may be provided as separate template structure information. The template structure information may be used for determining a relation between the locations and/or geometry of template structures and the locations and/or geometry of structures in the acquired MR image stack. This relation may then be used to generate warp information describing at least one transformation bringing the CT image stack in spatial correspondence with the acquired MR image stack.

The CT image stacks and the template structure information may form a template dataset that is handled by the Image Warping Engine 114. The template dataset may be selected from the Segmented Template Image Repository 118.

The Image Warping Engine 114, in some embodiments, takes a set of template MR image stacks from the Segmented Template Image Repository 118 and determines spatial deformations that would bring the template MR image stacks in spatial correspondence with the incoming MR image stack.

The set of template MR image stacks may be selected and included in the template dataset from the Segmented Template Image Repository 118 in order to retrieve MR image stacks that form a representative population of a region that is imaged in the acquired MR image stack. The selection may also be based on information of the persons who are imaged in the template MR image stacks, using information such as gender, age, weight, ethnicity, BMI, pathology, or any other parameter which may affect the results.

The Image Warping Engine 114 may use the segmentation of the incoming MR image stack as made by the Automatic Segmentation Engine 110. The template MR image stacks may be previously segmented. The segmentations may hold information of locations and/or geometry of structures and labels of such structures in the incoming MR image stack as well as the template MR image stacks.

For each of the selected template MR image stacks, the Image Warping Engine 114 may calculate a transformation based on the locations and/or geometry of corresponding structures in the template MR image stack and the incoming MR image stack in order for the structures to be spatially corresponding. The segmentations may thus drive the transformation of the template MR image stack in order to bring the template MR image stack in spatial correspondence with the incoming MR image stack.

According to one embodiment, utilizing the information of locations and/or geometry of structures in the acquired MR image stack and the template MR image stacks comprises performing non-rigid form matching between locations and/or geometry of structures in the acquired MR image stack and the template MR image stacks.

The relation between the template MR image stack and the incoming MR image stack may be even further improved after the segmented structures have been used in order to align the template MR image stack and the incoming MR image stack.

According to one embodiment, the improvement may comprise applying non-rigid image registration, for example matching an image similarity metric between the template MR image stack and the acquired MR image stack. This implies that the determining of spatial deformations may comprise both using segmentation of structures in the incoming MR image stack and the template MR image stack and using an image similarity metric. Hence, a very accurate spatial correspondence between the template MR image stack and the acquired MR image stack may be determined.

When it is determined how to bring the template MR image stack and the incoming MR image stack in spatial correspondence with each other a calculation for generating warp information, describing the transformation of the template MR image stack may be performed. The transformation may be deformation fields describing the transformation of the template MR image stack. Alternatively, the transformation may be a non-rigid transformation, a transformation matrix or any number of such transformations in combination, possibly describing the transformations of portions of the template MR image stack, whereas an interpolation may be used between the portions.

The template MR image stack may be actually deformed by the Image Warping Engine 114 in order to generate the warp information. However, according to an alternative, the warp information required for bringing the template MR image stack in spatial correspondence with the incoming MR image stack is determined without the actual spatial deformation of the template MR image stack being performed.

The Image Warping Engine 114, in some embodiments, warps each of the utilized CT image stacks from the Segmented Template Image Repository 118 using the generated warp information such that the shapes of its segmented structures overlap with the shapes of the automatically segmented structures generated by the Automatic Segmentation Engine for the incoming MR image stack, thereby generating a candidate synthetic CT image stack representing the incoming MR image stack. In one embodiment, the warping is achieved using known techniques from published image registration research.

In one embodiment of the Image Warping Engine 114, the space in between the structure shapes in the warped CT image stacks may be spatially translated to satisfy the new locations of the shapes while preserving smooth deformation in all parts of the image stack. In yet another embodiment, estimated deformation restrictions (i.e. elasticity, viscosity, stiffness, etc.) for various tissues may be taken into account during the deformation of tissue in between the structure shapes.

In yet another embodiment of the Image Warping Engine 114, an MR image stack from the Segmented Template Image Repository 118 may be warped in such way that a local image similarity metric between the incoming MR image stack and the warped MR image stack is optimized. The deformation field calculated from such warping may then be applied to the corresponding CT image stack from the Segmented Template Image Repository 118, which may generate a candidate synthetic CT image stack. In such embodiment the warping of the MR image stack from the Segmented Template Image Repository 118 may be initialized according to any of the mentioned embodiments and additional translation of the shapes of aligned segmented structures may be restricted.

The Image Warping Engine 114 need not necessarily perform warping of the template CT image stacks. Rather, a representation of the transformation to be made to the template CT image stack may be formed. This constitutes information of the relation between the template CT image stack to the acquired MR image stack, which may be used as input to how synthetic CT image stack is to be formed from the template CT image stacks, Image Fusion Engine The Image Fusion Engine 116, in some embodiments, fuses the candidate CT image stacks generated by the Image Warping Engine 114 into a final synthetic CT image stack. In one embodiment, such fusion may be performed by choosing or combining values from one or more of the candidate synthetic CT image stacks, which may be selected using a mathematical method (e.g. histogram based, median value, etc.), or by comparing imaging similarities between warped template MR image stacks and the incoming MR image stack, or by utilizing statistical or machine learning methods, or by any combination thereof. In yet another embodiment, such fusion includes calculating an average or median value of all selected candidate synthetic CT image stacks, or performing a calculation using information from one or more candidate synthetic CT image stacks. In yet another embodiment, such fusion is performed locally, using information at or in the nearby of a corresponding local region in one or more of the candidate synthetic CT image stacks. In yet another embodiment, the correspondingly warped MR image templates or the correspondingly warped template structures are utilized in the fusion process. In yet another embodiment, such fusion is achieved using a combination of the described techniques.

In yet another embodiment, the Image Fusion Engine 116 receives information about the warping to be applied to a template CT image stack such that when the Image Fusion Engine 116 determines that a portion of the template CT image stack is to be used in the fusion, the particular portion of the template CT image stack is warped. Hence, the entire template CT image stacks need not be warped.

In yet another embodiment, a single template CT image stack is provided and warp information is generated for the single template CT image stack. This may be relevant e.g. when using a template CT image stack that has been acquired from the same patient as is imaged in the incoming MR image stack. In such case, it may not be necessary to fuse information from a plurality of template CT image stacks. Rather, the synthetic CT image stack may be formed from the single template CT image stack.

Figure 3:
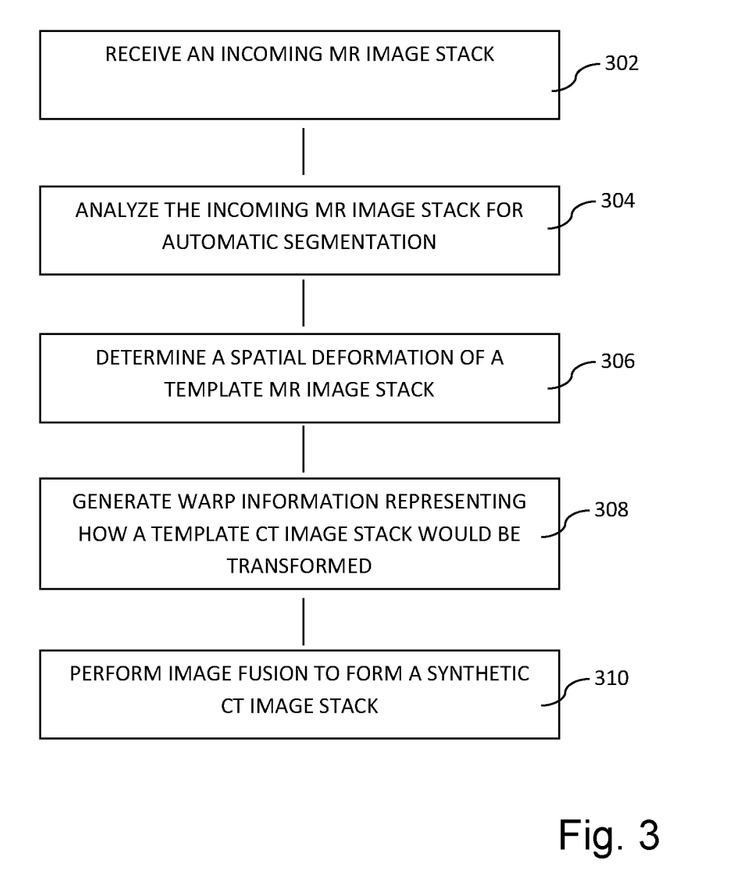
FIG. 3 is a flow chart illustrating a method according to an embodiment of the invention.

Referring now to FIG. 3, a flow chart for a method according to an embodiment of the invention will be described. The description of the method summarizes the method steps as described above in relation to the system.

The method thus comprises receiving an acquired or incoming MR image stack, step 302. The incoming MR image stack may be acquired by an MRI scanner.

The incoming MR image stack is sent to the Automatic Segmentation Engine for analyzing the incoming MR image stack so as to automatically segment the incoming MR image stack, step 304.

Utilizing the segmentation and template structure information, e.g. in the form of previously segmented template MR image stacks, it is determined how to bring the location and/or geometry of the template structures, e.g. as represented in the template MR image stack, into alignment with the location and/or geometry of similar structures in the incoming MR image stack. Further, the spatial correspondence between the template MR image stack and the incoming MR image stack may be further improved by determining how to deform the template MR image stack in order to optimize an image similarity metric between the template MR image stacks and the incoming MR image stack. Thus, a spatial deformation of the template MR image stack may be determined, step 306, representing a deformation that brings the template MR image stack in spatial correspondence with the incoming MR image stack.

The determined spatial deformation may constitute warp information, which is in turn applied to template CT image stacks, which are respectively correlated to template MR image stacks. The warp information may thus provide a representation of how the template CT image stacks would be transformed, step 308, in order to correspondingly bring the template CT image stacks into correspondence with the incoming MR image stack.

Finally, an image fusion is performed, step 310, in order to form a synthetic CT image stack based on fusioning of at least parts of the template CT image stacks after using the warp information, wherein the image fusion may e.g. take median or average value of the warped template CT image stacks or may stitch different parts of the warped template CT image stacks together.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms used herein should be interpreted as having a meaning that is consistent with their meaning in the context of this specification and the relevant art and will not be interpreted in an idealized or overly formal sense unless expressly so defined herein.

The foregoing has described the principles, preferred embodiments and modes of operation of the present invention. However, the invention should be regarded as illustrative rather than restrictive, and not as being limited to the particular embodiments discussed above. The different features of the various embodiments of the invention can be combined in other combinations than those explicitly described. It should therefore be appreciated that variations

The invention claimed is:

1. A computer-implemented method for generating synthetic electron density information based on an acquired magnetic resonance (MR) image stack, said method comprising:
analyzing, with a processor, the acquired MR image stack which is stored in a first memory location in order to automatically segment the acquired MR image stack such that structure information defining locations and/or geometry of structures in the acquired MR image stack is determined;
generating, with the processor, warp information for a template dataset, said template dataset comprising at least one template electron density information map and at least one template structure information, which is stored in a second memory location, said generating comprising utilizing said structure information and said at least one template structure information, wherein said at least one template structure information is configured to represent locations and/or geometry of template structures in order to determine transformations bringing the template structures in spatial correspondence with the structures in the acquired MR image stack, wherein said generated warp information describes at least one transformation bringing the at least one template electron density information map in spatial correspondence with the acquired MR image stack;
forming, with the processor, synthetic electron density information, which is stored in a third memory location, corresponding to the acquired MR image stack based on at least part of the at least one template electron density information map, wherein the at least part of the at least one template electron density information map is warped using the generated warp information, and
controlling radiation treatment based on a radiation treatment plan, wherein the synthetic electron density information provides attenuation information for forming the radiation treatment plan.

2. The computer-implemented method according to claim 1, wherein the synthetic electron density information is in the form of a synthetic computed tomography, CT, image stack and the at least one template electron density information map is a template CT image stack.

3. The computer-implemented method according to claim 1, wherein the generated warp information comprises non-rigid transformation of the at least one template electron density information map.

4. The computer-implemented method according to claim 1, wherein the generated warp information comprises deformation fields utilized in the transformations bringing the at least one template electron density information map in spatial correspondence with the acquired MR image stack.

5. The computer-implemented method according to claim 1, further comprising accessing a database in which template data is stored, and selecting a set of data from the database to constitute the template dataset.

6. The computer-implemented method according to claim 5, wherein the template data is stored in the database in association with information about a person, and wherein the selection of the set of data to constitute the template dataset is based on a combination of information including: gender, age, weight, ethnicity, body mass index, BMI, or pathology.

7. The computer-implemented method according to claim 1, wherein the analyzing of the acquired MR image stack is made in order to identify locations and/or geometry of at least one of or a part of: bone and skeleton parts, fat, muscle tissue, inner organs, intestines, bowels, colon, bladder, reproductive organs, brain regions, eyes, cochlea, sinuses, spine, mouth, nerves, glands, blood vessels, lungs, airways, heart, tumours or metastases, any type of markers, implants or prostheses, or any type of resection cavity or other effect from previous treatments or traumas.

8. The computer-implemented method according to claim 1, wherein a set of template electron density information maps are used and wherein said generated warp information describes transformations bringing each template electron density information map in the set of template electron density information maps in spatial correspondence with the acquired MR image stack, and
wherein said forming comprises fusioning, with the processor, at least parts of the set of template electron density information maps, wherein the at least parts of the set of template electron density information maps are warped using the generated warp information, to form synthetic electron density information corresponding to the acquired MR image stack.

9. The computer-implemented method according to claim 1, wherein the template dataset further comprises at least one template MR image stack and wherein said generating of warp information comprises determining, with the processor, spatial deformations of the at least one template MR image stack, said spatial deformations bringing the at least one template MR image stack in spatial correspondence with the acquired MR image stack, wherein the at least one template MR image stack has been segmented to identify template structure information representing locations and/or geometry of structures in the at least one template MR image stack, said spatial deformations comprising utilizing the structure information of the acquired MR image stack and the template structure information in order to bring the structures of the at least one template MR image stack to spatial correspondence with corresponding structures of the acquired MR image stack;
and wherein the at least one template electron density information map is associated to respective ones of the at least one template MR image stack to define the spatial and geometric relation between the at least one template MR image stack and the at least one template electron density information map, said generated warp information being based on the determined spatial deformations and said spatial and geometric relation.

10. The computer-implemented method according to claim 9, wherein the at least one template MR image stack and the at least one template electron density information map associated to respective ones of the at least one template MR image stack are arranged in close geometric registration to each other.

11. The computer-implemented method according to claim 9, wherein the determining of said spatial deformations further comprises, after said utilizing, improving, with the processor, the spatial correspondence of the at least one template MR image stack with the acquired MR image stack by applying non-rigid image registration between the at least one template MR image stack and the acquired MR image stack.

12. A computer program product comprising a non-transitory computer-readable medium with computer-readable instructions such that when executed on a processing unit the computer program product will cause the processing unit to perform the method according to claim 1.

13. A system for generating synthetic electron density information based on an acquired magnetic resonance (MR) image stack, said system comprising:
a processor;
an automatic segmentation software module, which is configured to cause the processor to analyze the acquired MR image stack such that structure information defining locations and/or geometry of structures in the acquired MR image stack is determined;
a warp software module, which is configured to cause the processor to generate warp information for a template dataset, said template dataset comprising at least one template electron density information map and at least one template structure information, said generating comprising utilizing said structure information and said at least one template structure information, wherein said at least one template structure information is being configured to represent locations and/or geometry of template structures in order to determine transformations bringing the template structures in spatial correspondence with the structures in the acquired MR image stack, wherein said generated warp information describes at least one transformation bringing the at least one template electron density information map in spatial correspondence with the acquired MR image stack;
a forming software module, which is configured to cause the processor to form synthetic electron density information corresponding to the acquired MR image stack based on at least part of the at least one template electron density information map, wherein the at least part of the at least one template electron density information map is warped using the generated warp information, wherein the automatic segmentation software module, the warp software module, and the forming software module are stored in a memory associated with the processor; and
a radiation treatment device for providing radiation treatment, wherein the radiation treatment device is configured to be controlled based on a radiation treatment plan, and wherein the synthetic electron density information provides attenuation information for forming the radiation treatment plan.

14. The system according to claim 13, further comprising a database in which the at least one template electron density information map and the at least one template structure information are stored.

* * * * *